United States Patent [19]

Rice et al.

[11] Patent Number: 4,598,153
[45] Date of Patent: Jul. 1, 1986

[54] METAPHIT, A SPECIFIC ACYLATING AGENT FOR THE [³H] PHENCYCLIDINE

[75] Inventors: Kenner C. Rice, Rockville, Md.; Michael F. Rafferty, Ann Arbor, Mich.; Arthur E. Jacobson, Potomac; Patricia Contreras, Bethesda, both of Md.; Thomas L. O'Donohue, Silver Spring; Ralph A. Lessor, Bethesda, both of Md.; Mariena V. Mattson, Wheaton, Md.

[73] Assignee: The United States of America as represented by the Department of Health and Human Services, Washington, D.C.

[21] Appl. No.: 683,428

[22] Filed: Dec. 19, 1984

[51] Int. Cl.⁴ ............................................. C07D 295/12
[52] U.S. Cl. .................................................... 546/229
[58] Field of Search ........................... 546/229; 514/331

[56] References Cited

U.S. PATENT DOCUMENTS 3,097,136 7/1963 Godefroi et al. .................... 546/192
4,196,185 4/1980 Focella et al. ....................... 514/317

OTHER PUBLICATIONS

CA 95:197196j, Itzhak et al.; Recepter Binding and Antinociceptive Prop. of PCP Opiate-Like Derivatives, 1981.
CA 94:174824e, Itzhak et al., New Analgesic Drugs from PCP, 1981.
CA 95:24749p, Johnson et al.; Synthesis of Amine Devatives of PCP 1981.
CA 96:97667r, Lin et al., PCP Conjugates to Antigenic Proteins and Enzymes, 1982.
CA 89:215409p, Krastinat et al., General-Substituted Cycloalkones, 1978.

Primary Examiner—Glennon H. Hollrah
Assistant Examiner—D. L. Dinner
Attorney, Agent, or Firm—John S. Roberts, Jr.

[57] ABSTRACT

A derivative of phencyclidine (1) bearing an isothiocyanate moiety of the meta position of the aromatic ring (2; Metaphit) has been synthesized and identified as a rapid and specific site-directed acylating agent of the [³H]-phencyclidine binding site in rat brain homogenates.

1 Claim, 3 Drawing Figures

METAPHIT, A SPECIFIC ACYLATING AGENT FOR THE [³H] PHENCYCLIDINE

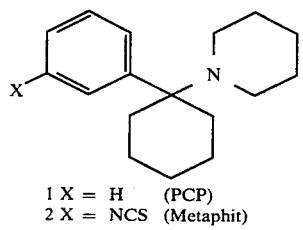

1 X = H (PCP)
2 X = NCS (Metaphit)

Additionally, the compound where X=NH$_2$ is a known derivative of phencyclidine.

Metaphit is the trivial name for 1-[1-(3-isothiocyanatophenyl)cyclohexyl]piperidine. The following related compounds are included within the ambit of this invention and are designated together with the parent as "Metaphit compounds."

Thiophit = 1-[1-(2-(4-isothiocyanato)thienyl)cyclohexyl]-piperidine; and

Ethylphit = N-[1-(m-isothiocyanatophenyl)cyclohexyl]-ethylamine; and

Bromophit = N-[1-(m-(α-bromoacetylamino)phenyl)-cyclohexyl]-ethylamine; and

Isopropylphit = N-[1-(m-isothiocyanatophenyl)cyclohexyl]-isopropylamine

The above compounds are utilized principally to block receptors of phencyclidine and related compounds such as ketamine, thus antagonizing the in vivo effects of phencyclidine, ketamine and other ligands which exert their pharmacological effects by interaction with phencyclidine receptors. Phencyclidine is described in Merck Index, 10th edition, page 1039, as: crystals, mp 46-46.5° ;, bp 135°-137° ; hydrochloride, C$_{17}$H$_{26}$ClN, Sernyl, Sernylan Crystals, mp 243°-244°. LD$_{50}$ orally in mice: 76.5 mg/kg, K. Bailey et al, J. Pharm. Pharmacol. 28:713 (1976); hydrobromide, crystals, mp 214°-218°; may produce serious psychologic disturbances; therapeutic category, anesthetic; therapeutic category (vet), analgesic, anesthetic.

The compound Ketamine is a dissociative anesthetic used clinically which produces schizophrenic-like and other psychotic states. Thus, the psychiatric use of Metaphit may be projected beyond PCP and Ketamine. The structure for Ketamine is as follows:

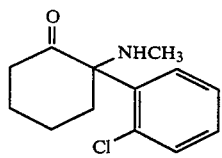

In Merck Index, 10th edition, page 761, Ketamine is described as: crystals from pentane-ether, mp 92°-93°, uv max (0.01 N NaOH in 95% methanol): 301, 276, 268, 261 nm 5.0, 7.0, 9.8, 10.5), pKa 7.5; hydrochloride, C$_{13}$H$_{17}$Cl$_2$NO, CI-581, Ketaject, Ketalar, Ketanest, Ketaset, Ketavet, Vetalar; white crystals, mp 262°-263°; soly in water: 20 g/100 ml; LD$_{50}$ mice, rats (adult): 224±4, 229±5 mg/kg i.p., E. J. Goldenthal, Toxicol. Appl. Pharmacol. 18:185 (1971); therapeutic category, general anesthetic; thera-peutic category (vet), anesthetic.

Ketamine is currently used as an anesthetic in the practice of medicine for certain situations such as burn cases and in small children and pregnant women. Ketamine has some effects in common with phencyclidine as a disassociative anesthetic and Metaphit may be useful as an antagonist for Ketamine anesthesia. Some side effects of Ketamine anesthesia are similar to those of phencyclidine abuse. A functional antagonist for Ketamine would therefore eliminate the side effects produced after Ketamine anesthesia. One further factor is that phencyclidine exerts its effects in the central nervous system by acting on receptor sites (analogous to the opiates) and Metaphit is a valuable research tool for this circuitry in the brain and greatly facilitates study of the structure and function of the phencyclidine recognition site in the central nervous system.

MATERIAL INFORMATION DISCLOSURE

The following patents are of interest: U.S. Pat. No. 3,097,136 Godefroi et al, phencyclidine, and U.S. Pat. No. 4,196,185 Focella et al. Relative to 4,196,185, this patent deals with development of an immunoassay for phencyclidine. Focella et al prepare a carboxylic acid derivative of phencyclidine and use this compound as a ligand to couple to bovine serum albumin. This drug, coupled with protein, can be used to generate antibodies against the phencyclidine derivatives. The phencyclidine derivative is a carboxylic acid and it is coupled in the standard way to bovine serum albumin using carbodiimide methodology. The coupling of this compound through an amide system is standard technique. A benzoic acid derivative which is used as the haptan will not couple in the absence of the carbodiimide reagent. The Metaphit, on the other hand, is a site directed acylating agent for phencyclidine receptors. The electrophilic function is already built into Metaphit as an isothiocyanate function. The inherent affinity of the phencyclidine carbon nitrogen skeleton causes binding to the receptor and then the electrophilic function already present in Metaphit, the isothiocyanate function, then forms a covalent bond with the receptors. Metaphit is a specific acylating agent for phencyclidine receptors to the exclusion of benzodiazepine receptors, opiate receptors, and QNB receptors.

The illicit use of phencyclidine (PCP) is a major problem in the United States that has rivaled the abuse of heroin and cocaine. The bizarre dissociative behavioral effects produced in humans by PCP range from schizophrenia-like states to violently aggressive behavior and self-mutilation. These effects have stimulated interest in the biochemical pharmacology of PCP and recent studies have described stereoselective, saturable binding sites in rat brain and other species. Despite some initial controversy concerning the pharmacological relevance of the site, a high degree of correlation between binding affinity and in vivo activity of several PCP-mimetics support the contention that the site is indeed a pharmacological receptor. The recent finding of an endogenous peptide with a binding affinity much greater than PCP for this site raises questions concerning the physiological function of these sites in the CNS and their involvement in neuropsychiatric states.

Recent efforts of the present inventors have resulted in the synthesis of compounds which specifically acylate mu and delta opioid receptor subtypes. In view of the relation between the [³H]PCP binding site and the putative sigma opiate receptor, there have been synthesized PCP derivatives bearing acylating and alkylating functional groups in an attempt to develop an affinity label for this recognition site which could prove to be of value in probing its role in the CNS and aid in isolation and characterization of the binding site proteins. The present invention is a synthesis and biochemical characterization of the first electrophilic acylating PCP derivative 1-[1-(3-isothiocyanatophenyl)cyclohexyl]piperidine, which is termed "Metaphit."

Metaphit was prepared from the known PCP analogue where $X=NH_2$ using standard procedures and was fully characterized by spectral data and combustion analysis. Binding experiments were conducted on freshly prepared rat hippocampal and striatal homogenates using an assay procedure adapted from Zukin et al, *Brain Res.* 258:277 (1983). All data were analyzed using the LIGAND program developed by Munson and Rodbard, *Anal. Biochem.* 107:220 (1980). Binding methodologies for other receptors were taken from Yamamura et al, *Proc. Nat. Acad. Sci. USA*, 71:1725 (1974); Paul et al, *Science*, 202:892 (1978); Gabrielevitz et al, *Life Sci.*, 26:89 (1980); and Itzhak et al, *Eur. J. Pharmacol.* 72:305 (1981). Comparison of displacement curves generated with untreated control tissue and tissue treated with 10 uM Metaphit revealed a significant loss of binding capacity in the treated tissue. Scatchard plots of the data show that Metaphit treatment results in a significant loss of sites without altering the affinity of the remaining sites [Kd for control, $1.14 \times 10^{-7}$ M, for treated $1.17 \times 10^{-7}$ M; Bmax for control, 2.96 pmoles/mg protein, for treated, 1.09 pmoles/mg protein]. In control experiments, substitution of Metaphit with PCP at various concentrations (10 to 50 uM) did not result in a significant loss of tissue binding, indicating that the washing procedure used was sufficient to remove any unbound ligand from the tissue. The percentage of binding sites which were acylated by Metaphit treatment was about the same in the hippocampus and striatum. Tissue homogenates prepared from rat hippocampus showed a 45% degree in binding after Metaphit exposure, and 50% of the sites in homogenates from striatum were Metaphit sensitive (see Table 1). In all cases a significant component of control [$^3$H] PCP binding sites remained intact following treatment with Metaphit, and no conditions were found which could produce a complete loss of binding. These results suggest that the [$^3$H] PCP binding site population consists of two subtypes with similar affinity for PCP which can be differentiated on the basis of their sensitivity to Metaphit. Variation of treatment time revealed that a 5 minute exposure was sufficient to label all susceptible sites, and longer treatments of up to 2 hours did not result in any additional loss of binding.

The extreme reactivity of Metaphit toward a subpopulation of sites was demonstrated by the requirement for high concentrations of added PCP to protect these sites. Only when the tissue homogenate (pooled striatum and hippocampus) was preincubated with 50 uM cold PCP prior to a brief (10minute) exposure to Metaphit (10 uM; 5° C.) was an attenuation observed in the number of sites acylated (25% decrease in sites, compared with a 49% loss when PCP was not included as a pretreatment). The results suggested that susceptible binding sites may contain a suitably located amino acid such as a lysine or cysteine residue, since isothiocyanates are particularly reactive toward amine and sulfhydryl nucleophiles. The reactivity of the isothiocyanate moiety was also a concern with respect to solution stability, since the Tris.HCl buffer used contains a primary amino group. The stability of Metaphit in Tris buffer was established experimentally, as was its rapid reaction with methylamine under the same conditions.

The acrylating specificity of Metaphit for the [$^3$H] PCP site was determined because PCP and its congeners have been reported to interact at cholingergic receptors and with opioid receptors and possess analgesic activity. Metaphit was found to displace [$^3$H] QNB (quinuclidinyl benzilate) from muscarinic receptors in rat brain homogenates with a potency equivalent to PCP, without a significant loss of QNB binding compared with control tissues (Table 1). Likewise, Metaphit competitively inhibited [$^3$H] dihydromorphine binding but no irreversible blockade of opioid receptors could be observed. Metaphit was inactive in all respects toward the [$^3$H]diazepam site. These data, coupled with the insensitivity of a portion of the [$^3$H]PCP binding sites, indicate that Metaphit is highly specific as a covalent labelling reagent.

In summary, the PCP congener Metaphit has been found to covalently modify a significant portion of the [$^3$H]PCP binding sites found in rat brain. The observation of differences of the action of Metaphit on binding sites in the striatum and hippocampus, that is, insensitivity of some of these sites to labelling, leaves open the possibility that the binding site pool is comprised of at least two different sites, perhaps with different pharmacological roles.

In Table 1 below, which shows the ability of Metaphit to reversibly and irreversibly antagonize binding of various brain receptor ligands, the ligand concentrations used were 8 nM [$^3$H]phencyclidine, 0.5 nM [$^3$H]QNB, 1 nM [$^3$H]dihydromorphine, and 5 nM [$^3$H]diazepam. The binding methodology for PCP was modified, the others were from known methods; i.e., Yamamura et al, supra, Paul et al, supra, Gabrielevitz et al, supra, and Itzhak et al, supra. Specific binding refers to the percent binding remaining in washed, treated tissue compared with similarly washed controls. IC50 values for Metaphit were estimated from competitive displacement curves.

TABLE 1

Ability of Metaphit to Reversibly and Irreversibly Antagonize Binding of Various Brain Receptor Ligands

| Ligand | Maximum % Alkylation by 10 uM Metaphit | $IC_{50}$, uM for Metaphit | $IC_{50}$, uM for PCP |
| --- | --- | --- | --- |
| [$^3$H]PCP | | | |
| Hippocampus | 45* | — | 0.075 |
| Striatum | 50* | — | 0.070 |
| [$^3$H]QNB | 0 | 19 | 25 |
| [$^3$H]Dihydromorphine | 0 | 11 | 13** |
| [$^3$H]Diazepam | 0 | >1000 | >200 |

*These average numbers are not statistically different
**Obtained from Itzhak et al, Eur. J. Pharmacol., 72:305 (1981)

Metaphit, 1-(1-(3-isothiocyanatophenyl)cyclohexyl)-piperidine, produced a dose-dependent decrease in the number of PCP receptors determined in brain homogenates from rats pretreated with Metaphit 24 hours before sacrifice as compared to control values. The same doses of Metaphit that decreased PCP binding also antagonized PCP-induced sterotypy and ataxia. This antagonism was evident 1 and 24 hours after Metaphit pretreatment and was dose-dependent. These results suggest that irreversible binding of Metaphit to PCP receptors antagonized PCP-induced sterotypy and ataxia. Thus, Metaphit is the first drug that directly antagonizes the behavioral effects of PCP by inhibiting the interaction with PCP receptors.

Phencyclidine (1-(1-phenylcyclohexyl)-piperidine, angel dust, PCP) was first synthesized as a general anesthetic by the Parke Davis Pharmaceutical Company. However, its use as an anesthetic was soon terminated because of psychological side effects, which could last more than 12 hours. PCP is currently a major drug of abuse due in part to its ability to produce euphoria, excitation and to alter perception in a bizarre manner. In addition, PCP can also produce violently aggressive behavior and a persistent psychosis. The PCP-induced psychosis is often referred to as schizophrenia-like because of the similarities between the symptoms of acute schizophrenia and the PCP psychosis. Indeed, it has even been suggested that the use of PCP instead of amphetamines would provide a better drug model for schizophrenia. Since the mechanism of action of PCP is not known, there is still no specific treatment for PCP intoxication and psychosis.

At least some of the pharmacological effects of PCP are thought to be mediated by PCP receptors. PCP receptors have a unique distribution, with highest concentrations in the hippocampus and cortex and high concentrations in the nucleus accumbens, all of which may be relevant to PCP's psychotomimetic properties. Also, the pharmacological relevance of PCP receptors is supported by reports that the ability of PCP analogs to generalize to PCP stimulus, induce sterotypy, and alter 2-deoxyglucose metabolism correlates well with their ability to bind to PCP receptors. However, there are conflicting reports on the correlation between the structural requirements for induction of ataxia and PCP receptor binding. Unfortunately, until now there has not been a selective PCP receptor antagonist available to determine whether binding to PCP receptors is necessary for pharmacological activity. A PCP receptor antagonist would not only be useful in evaluating which effects of PCP are mediated by PCP receptors but could also potentially be applied to the treatment of PCP intoxication or the psychotomimetic side effects of ketamine, a PCP-like anesthetic. The purpose of the present invention is to disclose the in vivo effects of Metaphit, a PCP analog that has been shown to acylate PCP receptors using in vitro binding assays.

EXAMPLE 1

Even though Metaphit has been shown to acylate PCP receptors when added to brain homogenates in vitro, it is still necessary to determine whether Metaphit acylates PCP receptors when administered in vivo. This question was answered by kinetic analysis of 3H-PCP binding in saline and Metaphit-pretreated rats. Male Sprague-Dawley rats (Taconic Farms, Germantown, NY) weighing 200–250 g were used in all experiments. All rats were anesthetized lightly with ether before a 20-gauge needle was used to make a hole in the skull of rats for intracerebroventricular (i.c.v.) injection of drugs. The animals were allowed at least 1 day to recover before being used. The 3H-PCP binding assay was adapted from the method of Quirion et al, *Peptides*, in press (see description of FIG. 1). Specific binding was defined as total radioligand bound minus the amount of radioligand bound in the presence of 30 uM PCP. Kd and Bmax values were determined by least squares regression. The results are expressed as the mean ±S.E. of at least three experiments.

Figure 1:
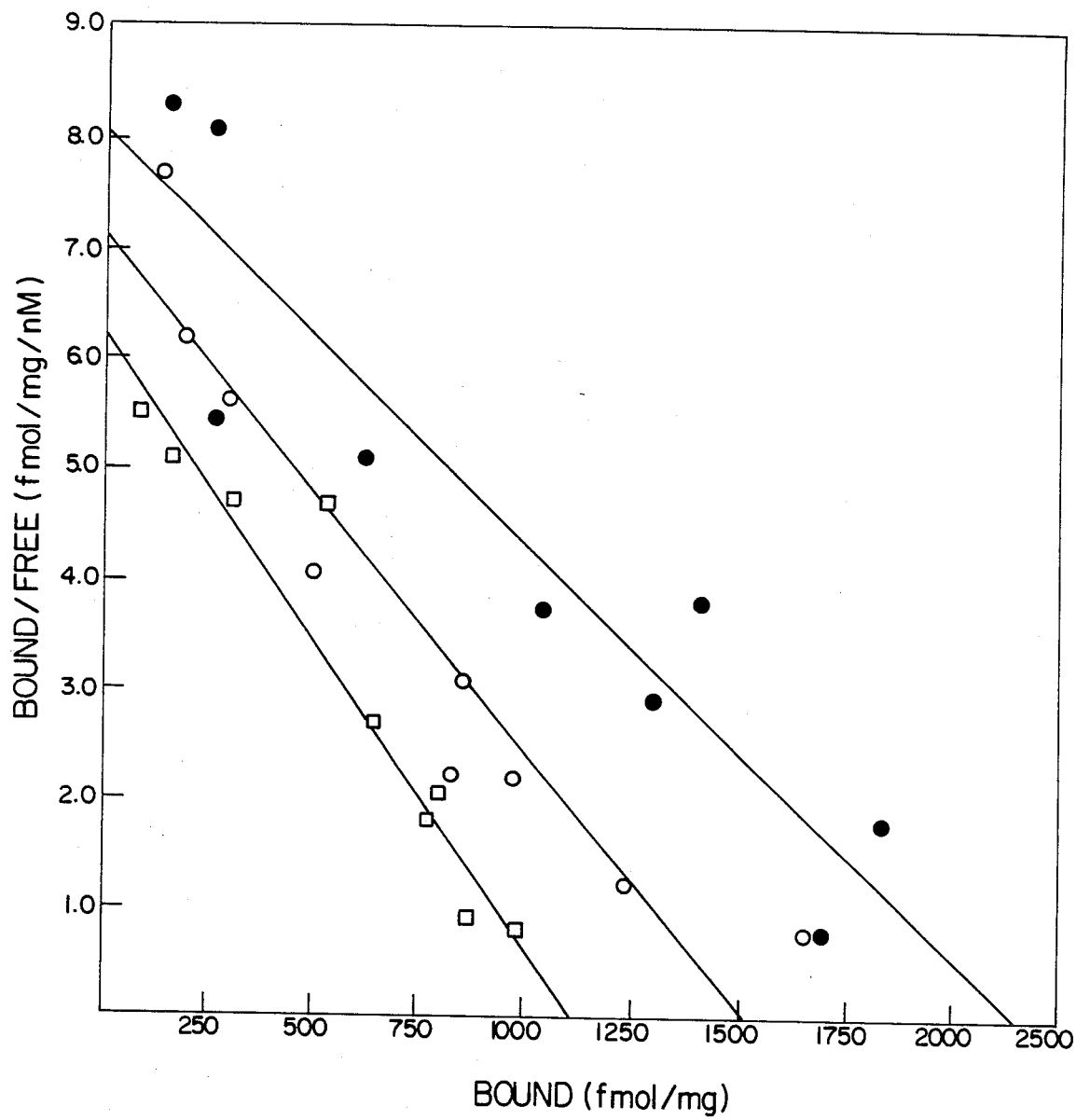
FIG. 1 shows examples of Scatchard plots of 3H-PCP binding in a crude membrane preparation from rats pretreated with saline (•), 1 umol/rat ( 0 ) or 2 umol/rat (□) of Metaphit. A crude membrane preparation in 5 mM Tris-HCl, pH 7.4 (Tris buffer) was prepared from the brains of rats pretreated with saline or Metaphit administered i.c.v. 24 hours before sacrifice. Incubation tubes, prepared in triplicate, contained a varying amount of 3H-PCP (New England Nuclear) made up in Tris buffer, 100 ul of membrane preparation and enough Tris buffer to make a total volume of 500 ul. The tubes were incubated for 50 minutes on ice and filtered through Whatman GF/B filters, which were presoaked for at least 2 hours in 0.05% polyethylenimine. The test tubes were washed twice and the filters once more with 4 ml of ice-cold Tris buffer. The filters were placed into scintillation vials containing 10 ml of Aquassure and radioactivity counted by liquid scintillation spectrometry. Protein concentrations were determined by the method of Lowry et al, *J. Biol. Chem.*, 193:254 (1951).

An example of Scatchard plots of 3H-PCP binding in membrane preparations from rats treated with saline or Metaphit 24 hours prior to sacrifice is shown in FIG. 1. There was no significant difference between the Kd values for 3H-PCP determined in rats pretreated with saline (Kd=237±8 nM), 1 umol/rat (Kd=237±8 nM) or 2 umol/rat of Metaphit (Kd=219±24 nM). However, there was a 25% and 40% decrease in the Bmax of 3H-PCP determined in rats pretreated with 1 umol/rat (Bmax=1550±70 pmol/mg) and 2 umol/rat (Bmax=1230±50 pmol/mg) of Metaphit, respectively, as compared to control (Bmax=2030±110 pmol/mg). These results indicate that Metaphit binds irreversibly to PCP receptors as administration of the drug changed only the number of binding sites without altering the affinity of binding in a dose-dependent manner and this effect was evident 24 hours after Metaphit pretreatment.

EXAMPLE 2

For the behavioral experiments concerning whether acylation of PCP receptors by Metaphit was associated with any changes in PCP's behavioral effects, rats were placed individually into 27×44×18 cm high plastic rat cages and allowed at least 1 hour to acclimate before testing began. PCP or Metaphit was administered by i.c.v. injection in 5 μl of saline. Stereotypy and ataxia were measured at 5 min intervals using a PCP rating scale. A rating of 5 was considered a 100% response. Dose-response curves of PCP represent behavioral ratings determined 5 min after PCP administration, the time of peak effect. At least 21 rats were used to determine each dose-response curve and ED50. ED50 values and dose-response curves were evaluated using the Finney assay (*Statistical Methods in Biological Assay*, 2nd ed., Hafner Publishing Co., N.Y, 1964) with the aid of a computer.

Figure 2:
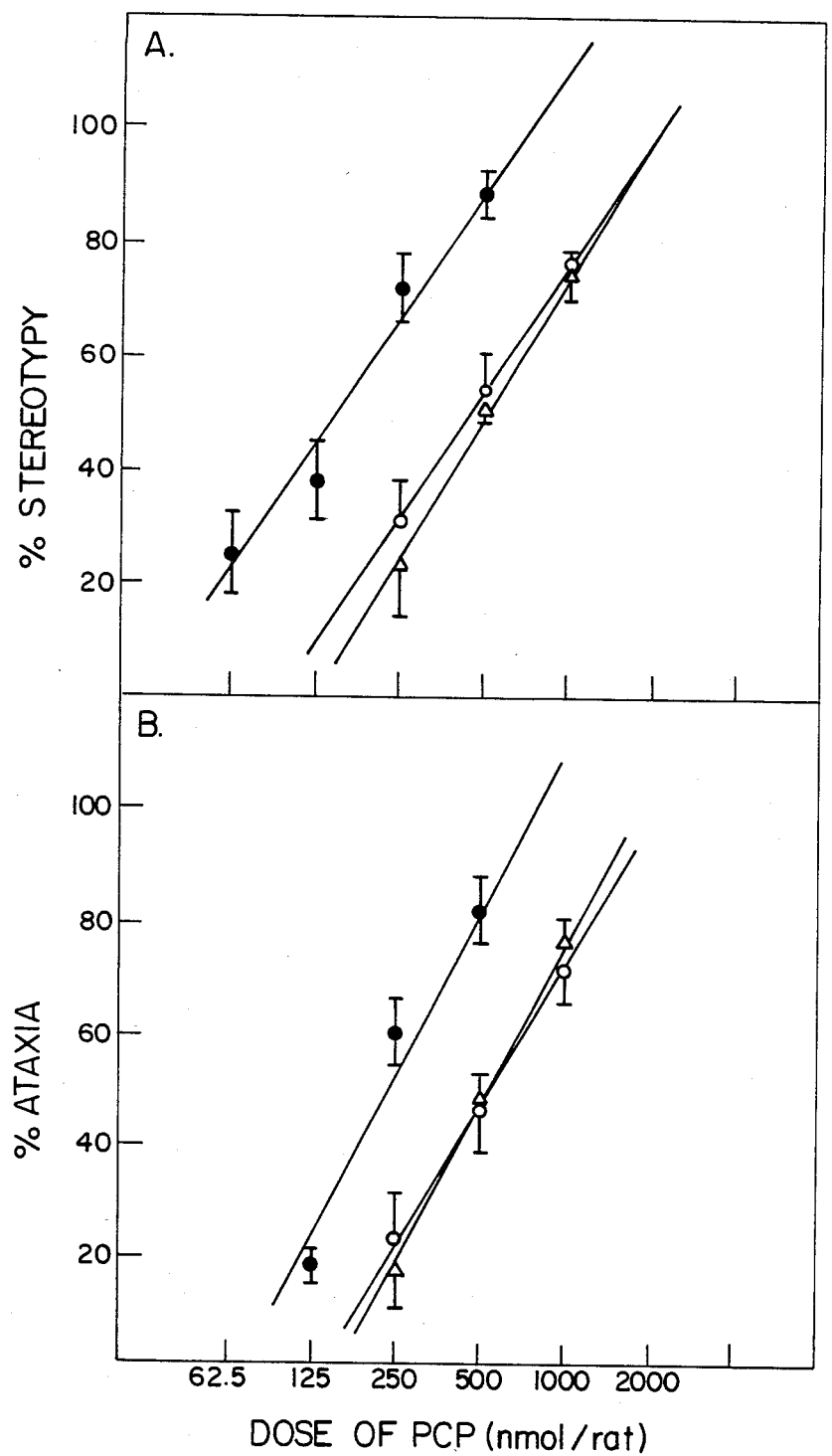
FIG. 2 shows PCP dose-response curves for (a) sterotypy and (b) ataxia determined in control rats (•), or 1 hour (Δ) or 24 hours ( 0 ) after i.c.v administration of 1 umol/rat of Metaphit.
Figure 3:
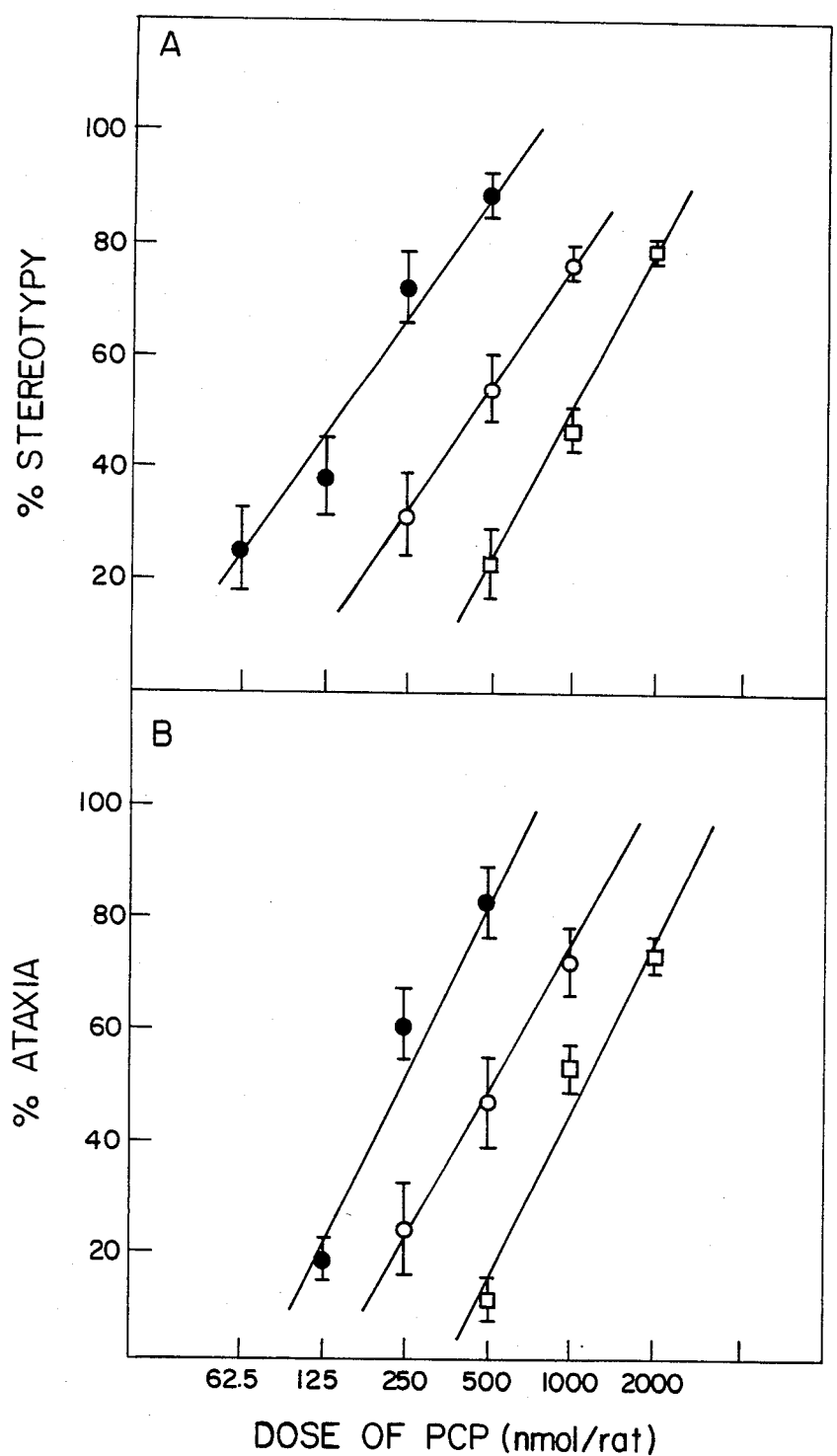
FIG. 3 shows PCP dose-response curves for (a) sterotypy and (b) ataxia determined in control rats (•) or 24 hours after i.c.v. administration of 1 umol/rat ( 0 ) or 2 umol/rat (□) of Metaphit.

Metaphit at a dose of 1 umol/rat did not produce any significant behavioral effects, but a dose of 2-8 umol/rat produced what appeared to be a calming effect as the rats generally remained stationary in a resting position in one spot, yet were not ataxic or catatonic and were generally alert. At these higher doses, a few rats exhibited qualitative changes similar to those exhibited by PCP treated rats, which were not quantitatively significant. The ability of PCP to induce stereotypy and ataxia was then evaluated 1 hour after 1 umol/rat of Metaphit. As illustrated in FIG. 2, PCP dose-response curves for stereotypy and ataxia were shifted significantly 3- and 2-fold, respectively, to the right of the control dose-response curves. This antagonism of PCP by 1 umol/rat of Metaphit was still evident 24 hours after Metaphit pretreatment, as the PCP dose-response curves for stereotypy and ataxia determined 24 hours after Metaphit pretreatment were not significantly different from those determined 1 hour after Metaphit pretreatment. The antagonism of PCP-induced stereotypy and ataxia was also dose-dependent (FIG. 3). Twenty-four hours after administration of 2 umol/rat of Metaphit, the PCP dose-response curves for stereotypy and ataxia were shifted 7- and 5-fold, respectively, to the right as compared to control.

These results show that acylation of PCP receptors by Metaphit results in antagonism of PCP-induced stereotypy and ataxia because doses of Metaphit that produced a significant decrease in the number of PCP receptors also antagonized the behavioral effects of PCP. In addition, these findings demonstrate that acylation of PCP receptors by Metaphit can be used to determine whether the effects of PCP are mediated by PCP receptors. The finding that Metaphit antagonized PCP-induced stereotypy is consistent with the reported correlation between PCP receptor binding and induction of stereotypy by PCP analogs. However, there are conflicting reports on the correlation between PCP receptor binding and induction of ataxia. The ability of Metaphit to antagonize PCP-induced ataxia shows that PCP receptors are involved in mediating PCP-induced ataxia but does not exclude the possibility that other mechanisms of action may be involved.

Dosage

The dosage of Metaphit or its related compounds noted in this application in relation to phencyclidine or ketamine is generally in the ratio of 1:2 to 2:1 effective weight percent with an optimum value of about 1:1 and the mode is by injection preferably i.p.

We claim:
1. Metaphit, 1-(1-(3-isothiocyanatophenyl)-cyclohexyl)piperidine.

* * * * *